United States Patent
Lee et al.

(10) Patent No.: US 9,365,833 B2
(45) Date of Patent: Jun. 14, 2016

(54) LEUCINE ZIPPER VARIANT AND USE THEREOF

(71) Applicant: Samsung Electronics Co., Ltd., Suwon-si, Gyeoniggi-do (KR)

(72) Inventors: Jung-Hoon Lee, Hwaseong-si (KR); Eunji Kang, Gyeonggi-do (KR); Hye Yoon Kang, Suwon-si (KR); Dongkyu Shin, Seongnam-si (KR); Jae Il Lee, Yongin-si (KR); Jieun Han, Gunpo-si (KR); Jung Min Lee, Seoul (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 68 days.

(21) Appl. No.: 14/502,088

(22) Filed: Sep. 30, 2014

(65) Prior Publication Data

US 2015/0094271 A1 Apr. 2, 2015

(30) Foreign Application Priority Data

Sep. 30, 2013 (KR) ......................... 10-2013-0116468

(51) Int. Cl.
*C12N 7/00* (2006.01)
*C07K 14/47* (2006.01)
*A61K 38/00* (2006.01)

(52) U.S. Cl.
CPC .............. *C12N 7/00* (2013.01); *C07K 14/4746* (2013.01); *A61K 38/00* (2013.01); *C07K 2319/10* (2013.01); *C07K 2319/73* (2013.01)

(58) Field of Classification Search
CPC ........................................................ C12N 7/00
See application file for complete search history.

(56) References Cited

U.S. PATENT DOCUMENTS

| | | | |
|---|---|---|---|
| 6,933,373 | B2 | 8/2005 | Conseiller et al. |
| 8,163,789 | B2 | 4/2012 | Doemling |
| 8,343,760 | B2 | 1/2013 | Lu et al. |
| 2002/0193561 | A1 | 12/2002 | Conseiller et al. |
| 2008/0280769 | A1 | 11/2008 | Doemling |
| 2011/0183917 | A1 | 7/2011 | Lu et al. |
| 2012/0309934 | A1 | 12/2012 | Jon et al. |
| 2012/0328692 | A1 | 12/2012 | Lu et al. |
| 2013/0005769 | A1 | 1/2013 | Storck et al. |

FOREIGN PATENT DOCUMENTS

| | | |
|---|---|---|
| JP | 2010-105992 A | 5/2010 |
| WO | WO 2008/106507 A2 | 9/2008 |

OTHER PUBLICATIONS

Brown et al., "Awakening guardian angels: drugging the p53 pathway", *Nature*, 9: 862-873 (2009).
Wade et al., "MDM2, MDMX and p53 in oncogenesis and cancer therapy", *Nature*, 13: 83-96 (2013).

*Primary Examiner* — Amber D Steele
(74) *Attorney, Agent, or Firm* — Leydig, Voit & Mayer, Ltd.

(57) ABSTRACT

A leucine zipper variant, a polynucleotide encoding the leucine zipper variant, a method of preparing a leucine zipper variant, a method of inhibiting HDM2- and/or HDMX using the leucine zipper variant, and a method of the prevention and/or treatment of cancer using the leucine zipper variant.

19 Claims, 13 Drawing Sheets

GCN4LZ  p53LZ1 p53LZ2  p53LZ3

```
                        SEQUENCE LISTING

<160> NUMBER OF SEQ ID NOS: 17

<210> SEQ ID NO 1
<211> LENGTH: 30
<212> TYPE: PRT
<213> ORGANISM: Artificial Sequence
<220> FEATURE:
<223> OTHER INFORMATION: Synthetic (Leucine zipper GCN4)

<400> SEQUENCE: 1

Arg Met Lys Gln Leu Glu Asp Lys Val Glu Glu Leu Leu Ser Lys Asn
1               5                   10                  15

Tyr His Leu Glu Asn Glu Val Ala Arg Leu Lys Lys Leu Val
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: Synthetic (Leucine zipper variant p53LZ2)

<400> SEQUENCE: 2

Arg Met Lys Gln Leu Glu Asp Lys Val Gly Glu Leu Leu Phe Ser Asn
1               5                   10                  15

Tyr Trp Leu Glu Leu Glu Val Ala Arg Leu Lys Lys Leu Val
            20                  25                  30

<210> SEQ ID NO 3
<211> LENGTH: 96
<212> TYPE: DNA
<213> ORGANISM: Artificial Sequence
<220> FEATURE:
<223> OTHER INFORMATION: Synthetic (nucleotide sequence encoding leucine
      zipper variant p53LZ2)
<220> FEATURE:
<221> NAME/KEY: misc_feature
<222> LOCATION: (1)..(3)
<223> OTHER INFORMATION: start codon
<220> FEATURE:
<221> NAME/KEY: misc_feature
<222> LOCATION: (4)..(93)
<223> OTHER INFORMATION: coding gene
<220> FEATURE:
<221> NAME/KEY: misc_feature
<222> LOCATION: (94)..(96)
<223> OTHER INFORMATION: stop codon
```

<400> SEQUENCE: 3
atgcgcatga aacagctgga agataaagtg ggcgaactgc tgtttagcaa ctattggctg    60
gaactggaag tggcgcgcct gaaaaaactg gtgtaa                              96

<210> SEQ ID NO 4
<211> LENGTH: 72
<212> TYPE: PRT
<213> ORGANISM: Artificial Sequence
<220> FEATURE:
<223> OTHER INFORMATION: Synthetic (WT p53)

<400> SEQUENCE: 4

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro
65                  70

<210> SEQ ID NO 5
<211> LENGTH: 9
<212> TYPE: PRT
<213> ORGANISM: Artificial Sequence
<220> FEATURE:
<223> OTHER INFORMATION: Synthetic (TAT peptide)

<400> SEQUENCE: 5

Arg Lys Lys Arg Arg Gln Arg Arg Arg
1               5

<210> SEQ ID NO 6
<211> LENGTH: 16
<212> TYPE: PRT
<213> ORGANISM: Artificial Sequence
<220> FEATURE:
<223> OTHER INFORMATION: Synthetic (MTS (membrane translocating
      sequence))

<400> SEQUENCE: 6

Ala Ala Val Ala Leu Leu Pro Ala Val Leu Leu Ala Leu Leu Ala Pro
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: Synthetic (MTS fragment)

<400> SEQUENCE: 7

Ala Ala Val Ala Leu Leu Pro
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic (MTS fragment)

```
<400> SEQUENCE: 8

Ala Val Leu Leu Ala Leu Leu Ala Pro
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic (NLS (nuclear localization sequence))

<400> SEQUENCE: 9

Lys Lys Lys Arg Lys
1               5

<210> SEQ ID NO 10
<211> LENGTH: 4
<212> TYPE: PRT
<213> ORGANISM: Artificial Sequence
<220> FEATURE:
<223> OTHER INFORMATION: Synthetic (NLS (nuclear localization sequence))

<400> SEQUENCE: 10

Lys Lys Lys Arg
1

<210> SEQ ID NO 11
<211> LENGTH: 6
<212> TYPE: PRT
<213> ORGANISM: Artificial Sequence
<220> FEATURE:
<223> OTHER INFORMATION: Synthetic (NLS (nuclear localization sequence))

<400> SEQUENCE: 11

Lys Lys Lys Arg Lys Arg
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic (NLS (nuclear localization sequence))

<400> SEQUENCE: 12

Arg Arg Arg Arg Arg
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic (NLS (nuclear localization sequence))

<400> SEQUENCE: 13

Arg Arg Arg Arg Arg Arg
1               5

<210> SEQ ID NO 14
<211> LENGTH: 21
<212> TYPE: PRT
<213> ORGANISM: Artificial Sequence
<220> FEATURE:
<223> OTHER INFORMATION: Synthetic (MTS-NLS fusion peptide)
```

```
<400> SEQUENCE: 14

Ala Ala Val Ala Leu Leu Pro Ala Val Leu Leu Ala Leu Leu Ala Pro
1               5                   10                  15

Lys Lys Lys Arg Lys
            20

<210> SEQ ID NO 15
<211> LENGTH: 12
<212> TYPE: PRT
<213> ORGANISM: Artificial Sequence
<220> FEATURE:
<223> OTHER INFORMATION: Synthetic (pDIQ)

<400> SEQUENCE: 15

Glu Thr Phe Glu His Trp Trp Ser Gln Leu Leu Ser
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Synthetic (pMI)

<400> SEQUENCE: 16

Thr Ser Phe Ala Glu Tyr Trp Asn Leu Leu Ser Pro
1               5                   10

<210> SEQ ID NO 17
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(10)
<223> OTHER INFORMATION: Xaa is Gly or Glu
<220> FEATURE:
<221> NAME/KEY: misc_feature
<222> LOCATION: (14)..(14)
<223> OTHER INFORMATION: Xaa is Phe or Ser
<220> FEATURE:
<221> NAME/KEY: misc_feature
<222> LOCATION: (15)..(15)
<223> OTHER INFORMATION: Xaa is Ser or Lys
<220> FEATURE:
<221> NAME/KEY: misc_feature
<222> LOCATION: (18)..(18)
<223> OTHER INFORMATION: Xaa is Trp or His
<220> FEATURE:
<221> NAME/KEY: misc_feature
<222> LOCATION: (21)..(21)
<223> OTHER INFORMATION: Xaa is Leu or Asn

<400> SEQUENCE: 17

Arg Met Lys Gln Leu Glu Asp Lys Val Xaa Glu Leu Leu Xaa Xaa Asn
1               5                   10                  15

Tyr Xaa Leu Glu Xaa Glu Val Ala Arg Leu Lys Lys Leu Val
            20                  25                  30
```

LEUCINE ZIPPER VARIANT AND USE THEREOF

CROSS-REFERENCE TO RELATED APPLICATIONS

This application claims the benefit of Korean Patent Application No. 10-2013-0116468 filed on Sep. 30, 2013 in the Korean Intellectual Property Office, the entire disclosure of which is incorporated by reference.

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: 5,557 bytes ASCII (Text) file named "718469_ST25.TXT," created Sep. 30, 2014.

BACKGROUND OF THE INVENTION

1. Field of the Invention

Provided are a leucine zipper variant, a polynucleotide encoding the leucine zipper variant, a method of preparing a leucine zipper variant, a method of inhibiting HDM2 and/or HDMX using the leucine zipper variant, and a method of the prevention and/or treatment of cancer using the leucine zipper variant.

2. Description of the Related Art

HDM2 and/or HDMX (i.e., HDM4), a negative regulator of tumor suppressor p53, promotes p53 ubiquitination to mediate the intracellular degradation of p53 by proteasome. HDM2 and/or HDMX is overexpressed in various kinds of cancer, and recognizes the p53 N-terminus TAD (transcription activation domain) by direct PPI (protein-protein interaction). Accordingly, attempts have been and are being made to develop antagonists useful for cancer therapy which inhibit the PPI between HDM2 and/or HDMX and p53 not only to prevent intracellular p53 degradation but also to reactivate p53.

SUMMARY

An embodiment provides a leucine zipper variant comprising at least one amino acid substitution selected from the group consisting of substitutions at positions 10, 14, 15, 18 and 21 of SEQ ID NO: 1. Another embodiment provides a polynucleotide encoding the leucine zipper variant.

Another embodiment provides an HDM2 and/or HDMX inhibitor (e.g., a pharmaceutical composition), including the leucine zipper variant as an active ingredient.

Another embodiment provides a method of inhibiting HDM2 and/or HDMX including administering the leucine zipper variant to a subject in need thereof.

Another provides a pharmaceutical composition for the prevention and/or treatment of cancer, including the leucine zipper variant as an active ingredient.

Another embodiment provides a method of preventing and/or treating a cancer, including administering the leucine zipper variant to a subject in need thereof.

BRIEF DESCRIPTION OF THE DRAWINGS

The embodiments described above and other objects, features and other advantages of the present invention will be more clearly understood from the following detailed description taken in conjunction with the accompanying drawings, in which.

DESCRIPTION OF THE PREFERRED EMBODIMENTS

One embodiment provides a leucine zipper variant. The leucine zipper variant has at least one substitution mutation which takes place at an amino acid residue that is externally exposed in the tertiary structure of a leucine zipper and has significant influence on the affinity to HDM2 (i.e., human double minute 2 homolog)/HDMX (i.e., HDM4; human homolog of murine double minute 4) but not on the conformational characteristics of the leucine zipper, thereby being characterized by an increased affinity to HDM2/ HDMX while retaining the structural stability of a wild-type leucine zipper (e.g., high Tm values, high α-helicity, and protease resistance).

Figure 12:
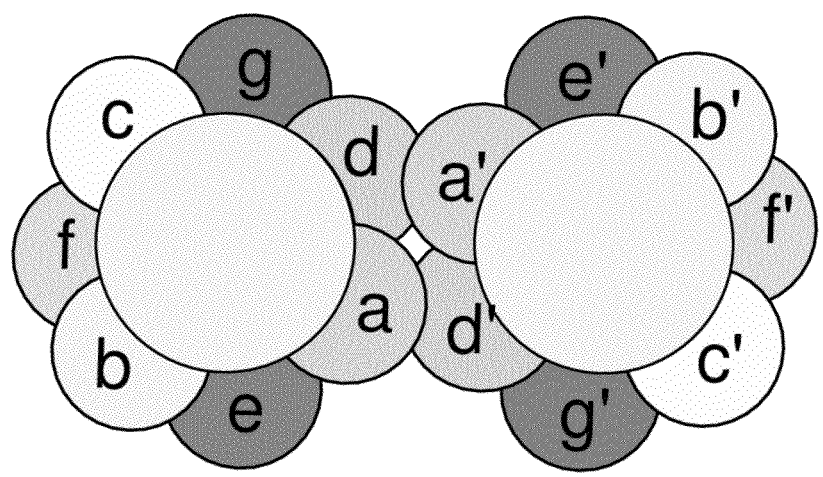
FIG. 12 is a helical wheel diagram, of a leucine zipper, where "d" represent the amino acid leucine, arranged with other amino acids on two parallel alpha helices.

A leucine zipper (LZ) is a common three-dimensional structural motif in proteins. These motifs are usually found as part of a DNA-binding domain in various transcription factors, and are therefore involved in regulating gene expression. The leucine zipper is a super-secondary structure that functions as a dimerization domain, and its presence generates adhesion forces in parallel alpha helices. A single leucine zipper consists of multiple hydrophobic leucine residues (at 'd' position; see FIG. 12) at approximately 7-residue intervals, which form an amphipathic alpha helix with a hydrophobic region (accounted for by the leucine residues) running along one side. Two, identical or different leucine hydrophobic regions of helices interact with each other to form a homo- or heterodimer in a zipper structure. As described above, leucine zippers are advantageously superior in stability and safety in vivo or in vitro because of their high Tm values, high α-helicity and protease resistance.

The leucine zipper variant may form a dimeric structure in which two identical or different leucine zipper single strands (alpha-helices) bind to each other at hydrophobic leucine regions. For example, the leucine zipper may be selected from the group consisting of homodimers of leucine zipper single strands, where each leucine zipper single strand includes leucine at d positions. The leucine zipper variant may be a homodimer variant of GCN4 (RMKQLEDKVE ELLSKNYHLE NEVARLKKLV; SEQ ID NO: 1; where leucine residues are at d positions) and the like.

When a mutation (e.g., substitution mutation) is applied to at least one of the amino acid residues of the leucine zipper in accordance with the present disclosure (except for leucine residues positioned at 7-residue intervals which is necessary for the structural integrity of leucine zipper), the leucine zipper variant has increased affinity to HDM2/ HDMX, while retaining the leucine zipper conformation, so that it can function as a HDM2/ HDMX double inhibitor.

One embodiment provides a leucine zipper variant in which one or more amino acids are different from wild-type counterparts by substitution (that is, at least one amino acid of wild-type leucine zipper is substituted with a different amino acid). The substitution takes place on one or more amino acids other than the leucine residues at 7-residue intervals. For example, in the case of GCN4 which is a leucine zipper having a single stranded alpha helix including the amino acid sequence set forth in SEQ ID NO. 1, amino acid substitutions are possible at one or more positions selected from the group consisting of positions 10, 14, 15, 18 and 21 of each alpha helix (SEQ ID NO: 1). For example, the leucine zipper variant may be a polypeptide comprising SEQ ID NO: 17, which is identical to SEQ ID NO: 1 except that positions 10, 14, 15, 18, and 21 are variable positions reflecting the points of substitution in the sequence. In one embodiment, the substitution may occur at positions 10 and 15, and optionally at one or more positions selected from the group consisting of positions 14, 18 and 21. For example, the leucine zipper variant may include SEQ ID NO: 1 with at least one mutation selected from the group consisting of substitutions of:

(a) glutamic acid (E) with glycine (G) at position 10 of the amino acid sequence of SEQ ID NO: 1;

(b) lysine (K) with serine (S) at position 15 of the amino acid sequence of SEQ ID NO: 1;

(c) serine (S) with phenylalanine (F) at position 14 of the amino acid sequence of SEQ ID NO: 1;

(d) histidine (H) with tryptophan (W) at position 18 of the amino acid sequence of SEQ ID NO: 1; and (e) asparagine (N) with leucine (L) at position 21 of the amino acid sequence of SEQ ID NO: 1.

In one embodiment, the leucine zipper variant may include SEQ ID NO: 1 with the following substitutions:

(a) glutamic acid (E) with glycine (G) at position 10 of the amino acid sequence of SEQ ID NO: 1; and (b) lysine (K) with serine (S) at position 15 of the amino acid sequence of SEQ ID NO: 1.

That is, the leucine zipper in accordance with an embodiment includes glycine (G) and serine (S), instead of glutamic acid (E) and lysine (K), at positions 10 and 15, respectively, of the amino acid sequence of SEQ ID NO: 1.

In another embodiment, the leucine zipper variant may include SEQ ID NO: 1 with the following substitutions:

(a) glutamic acid (E) with glycine (G) at position 10 of the amino acid sequence of SEQ ID NO: 1; and (b) lysine (K) with serine (S) at position 15 of the amino acid sequence of SEQ ID NO: 1, and optionally at least one mutation selected from the following substitutions:

(c) serine (S) with phenylalanine (F) at position 14 of the amino acid sequence of SEQ ID NO: 1;

(d) histidine (H) with tryptophan (W) at position 18 of the amino acid sequence of SEQ ID NO: 1; and (e) asparagine (N) with leucine (L) at position 21 of the amino acid sequence of SEQ ID NO: 1.

That is, the leucine zipper variant of another embodiment may include a variant of SEQ ID NO: 1 having glycine (G) instead of glutamic acid (E) at position 10 of the amino acid sequence of SEQ ID NO: 1, serine (S) instead of lysine (K) at position 15, phenylalanine (F) instead of serine (S) at position 14, and/or tryptophan (W) instead of histidine (H) at position 18, and/or leucine (L) instead of asparagine (N) at position 21.

For example, the leucine zipper variant can be a polypeptide comprising SEQ ID NO: 17 wherein
position 10 is glycine (G) or glutamic acid (E);
position 14 is phenylalanine (F) or serine (S);
position 15 is serine (S) or lysine (K);
position 18 is tryptophan (W) or histidine (H); and/or
position 21 is leucine (L) or asparagine (N);
provided that SEQ ID NO: 17 is not identical to SEQ ID NO: 1.

SEQ ID NO: 17 is represented by the following sequence:

```
Arg Met Lys Gln Leu Glu Asp Lys Val Xaa Glu Leu

Leu Xaa Xaa Asn Tyr Xaa Leu Glu Xaa Glu Val Ala

Arg Leu Lys Lys Leu Val
```

SEQ ID NO: 17 differs from SEQ ID NO: 1 in at least one of positions 10, 14, 15, 18, or 21. In other words, the leucine zipper polypeptide variant of SEQ ID NO: 17 does not comprise glutamic acid (E) at position 10, serine (S) at position 14, lysine (K) at position 15, histidine (H) at position 18 and asparagine (N) at position 21 at the same time. In another embodiment, the leucine zipper variant comprises SEQ ID NO: 17 comprising glycine (G) at position 10; serine (S) at position 15; phenylalanine (F) at position 14; tryptophan (W) at position 18; and/or leucine (L) at position 21.

When a mutation, such as substitution or deletion, takes place on amino acid residues at position 16 (N), 20 (E), 22 (E), and/or 24 (A), the leucine zipper variant exhibits decreased affinity to HDM2/ HDMX, thereby preventing the leucine zipper variant from achieving the desired inhibitory effect on HDM2/ HDMX. Therefore, the leucine zipper variant is characterized in that the amino acid residues at positions 16, 20, 22, and 24 of the amino acid sequence of SEQ ID NO: 1 are not mutated.

The leucine zipper variant of the present invention is characterized by high affinity to HDM2 and/or HDMX, with the retention of the structure and stability of the wild-type leucine zipper. The leucine zipper variant of the present invention may exhibit a binding affinity (Kd) to HDM2 of 100 nM or less, 50 nM or less, 30 nM or less, or 20 nM or less, for example, from 0.1 to 100 nM, from 0.1 to 50 nM, from 0.1 to 30 nM, or from 0.1 to 20 nM. With regard to HDMX, the leucine zipper variant may exhibit binding affinity (Kd) of 200 nM or less, 150 nM or less, 120 nM or less, or 100 nM or less, for example, from 0.1 to 200 nM, from 0.1 to 150 nM, from 0.1 to 120 nM, or from 0.1 to 100 nM.

In another embodiment, the leucine zipper variant may include the amino acid sequence of SEQ ID NO: 2 (RMKQLEDKVG ELLFSNYWLE LEVARLKKLV).

Figure 1:
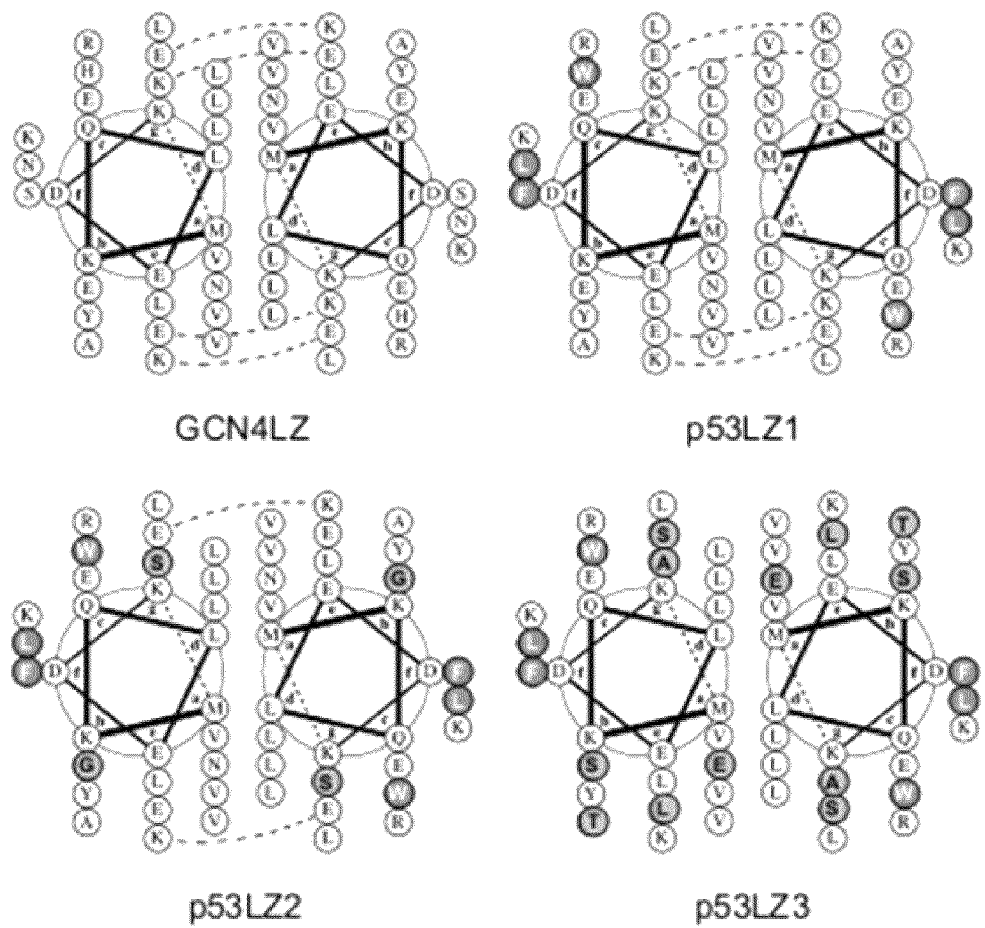
FIG. 1 is an illustration of leucine zipper variant designs according to one embodiment.

Also provided herein is a dimer comprising two alpha helices, each comprising a leucine zipper variant as described herein. A dimeric leucine zipper variant including two alpha helices, each including the amino acid sequence of SEQ ID NO: 2, is shown in FIG. 1 (indicated as p53LZ2).

In another embodiment, the leucine zipper variant may further include a cell-penetrating peptide (CPP). As used herein, the term "cell-penetrating peptide" refers to a peptide that is capable of penetrating a cell membrane. So long as it is able to penetrate into cell membranes, any peptide may be used For example, the CPP may be selected from the group consisting of:

TAT peptide (RKKRRQRRR; SEQ ID NO: 5),
a membrane translocating sequence (MTS; e.g., AAVALL-PAVLLALLAP (SEQ ID NO: 6));
an MTS fragment (a fragment having 7 to 16 consecutive amino acids within the amino acid sequence of MTS; e.g., AAVALLP (SEQ ID NO: 7), AVLLALLAP (SEQ ID NO: 8), etc.), and
a fusion peptide (e.g., AAVALLPAVLLALLAPKKKRK (SEQ ID NO: 14)) of MTS or MTS fragment with a nuclear localization sequence (NLS; e.g., KKKRK (SEQ ID NO: 9), KKKR (SEQ ID NO: 10), KKKRKR (SEQ ID NO: 11), RRRRR (SEQ ID NO: 12), RRRRRR(SEQ ID NO: 13)).

The cell-penetrating peptide may be linked (e.g., fused or covalently linked) to either or both of the C- and N-terminus, and/or a linkable amino acid residue of the leucine zipper peptide. The leucine zipper variant conjugated with a cell-penetrating peptide can be more effectively delivered into cells, thereby exhibiting higher inhibitory activity against HDM2 and HDMX and/or anticancer effect.

The leucine zipper variant may not be naturally occurring.

HDM2 and HDMX are negative regulators of p53 found in humans, functioning both as an E3 ubiquitin ligase that recognizes the N-terminal trans-activation domain (TAD) of the p53 tumor suppressor and an inhibitor of p53 transcriptional activation. The HDM2 may be encoded by the nucleotide sequence of NM_001145336 (cDNA) or may include the amino acid sequence of NP_002383, but not be limited thereto. The HDMX may be encoded by the nucleotide sequence of NM_001204171 (cDNA) or may include the amino acid sequence of NP_001191100, but not be limited thereto.

The leucine zipper variant exhibits higher affinity (binding force) to HDM2/ HDMX than p53 (wild-type), thereby effectively competing with p53 (wild-type), to prevent the HDM2/HDMX-mediated proteosomal degradation of p53. Therefore, the leucine zipper variant acts as a dual inhibitor of HDM2/ HDMX. Furthermore, the leucine zipper variant activates the tumor suppression function of p53 by restraining HDM2/ HDMX from binding to the tumor suppressor p53 and degrading p53. Thus, the leucine zipper variant has an anticancer activity The leucine zipper variant polypeptide can comprise additional amino acids flanking the variant of SEQ ID NO: 1 (e.g., SEQ ID NO: 17 or SEQ ID NO: 2), provided they do not eliminate the ability of the polypeptide to bind to HDM2 and HDMX. The flanking residues can be any suitable size. Typically, the leucine zipper variant polypeptide can have fewer than [insert ranges of overall size, e.g., fewer than 100 amino acids, such as fewer than 50 amino acids, or fewer than 25 amino acids]. Another embodiment provides a pharmaceutical composition for inhibiting HDM2 and/or HDMX comprising the leucine zipper variant polypeptide as an active ingredient. Another embodiment provides a method of inhibiting HDM2 and/or HDMX, comprising administering the leucine zipper variant polypeptide to a subject in need of HDM2 and/or HDMX inhibition (e.g., a subject with a disease associated with HDM2 and/or HDMX expression, such as cancer). The leucine zipper variant may be used in a pharmaceutically effective amount, which can be determined by the skilled medical practitioner or medical researcher. The method may further include identifying a subject in need of the inhibition of HDM2 and/or HDMX before the administration. The step of identifying may be conducted by any manners and/or methods known to relevant field for identifying whether or not a subject needs the inhibition of HDM2 and/or HDMX, for example through the analysis of a biological sample provided by a subject to detect HDM2 and/or HDMX overexpression or to detect a disease associated with HDM2 and/or HDMX expression.

In another aspect, provided is a method of preventing and/or treating a cancer, including administering the leucine zipper variant to a subject in need of preventing and/or treating a cancer. The leucine zipper variant may be used in a pharmaceutically effective amount, which can be determined by the skilled medical practitioner or medical researcher. This method may further include identifying a subject in need of the prevention and/or treatment of a cancer before the administration. The step of identifying may be conducted by any manners and/or methods known to relevant field for identifying whether or not a subject needs the prevention and/or treatment of a cancer. For example, the step of identifying may include diagnosing whether the subject has a cancer by genetic screening, cell culture analysis, or physical examination, or identifying that the subject is diagnosed as a cancer patient.

In the present invention, the subject or patient is intended to encompass all animals that need the intracellular delivery of the cytotoxic drug, and cells derived therefrom. For example, all mammals including primates such as humans and monkeys, and rodents such as mice and rats, cells or tissues derived (isolated) therefrom, and cultures of the cells or tissues may fall into the scope of the subject. By way of example, person suffering from with cancer, or at risk of cancer, or cancer cells or tissues derived (isolated) from the person, or a culture thereof may be a subject.

The cancer may be associated with inactivated and/or suppressed p53. The cancer may be solid cancer or blood cancer. Examples of the cancer include squamous cell carcinoma (e.g., squamous cell carcinoma of lung), squamous cell carcinoma (e.g., small-cell lung cancer, non-small-cell lung cancer, adrenocarcinoma of lung, squamous cell carcinoma of lung, etc.), peritoneal cancer, skin cancer, skin or intraocular melanoma, rectal cancer, perianal cancer, esophagus cancer, small intestine cancer, endocrine gland cancer, parathyroid cancer, adrenal cancer, soft-tissue sarcoma, urethral cancer, chronic or acute leukemia, lymphocytic lymphoma, hepatoma, gastrointestinal cancer, gastric cancer, pancreatic cancer, glioblastoma, cervical cancer, ovarian cancer, liver cancer, bladder cancer, hepatocellular adenoma, breast cancer, colon cancer, colorectal carcinoma, large intestine cancer, endometrial carcinoma or uterine carcinoma, salivary gland tumor, kidney cancer, prostate cancer, vulvar cancer, thyroid cancer, head or neck cancer, brain cancer, osteosarcoma, and a combination thereof The cancer may include a metastatic cancer as well as a primary cancer. For example, the cancer to be prevented and/or treated may be selected from the group consisting of osteosarcoma, colorectal carcinoma, breast carcinoma, lung carcinoma, and the like.

With regard to the prophylactic and/or therapeutic effect on cancer, administration of the leucine zipper variant may alleviates the malignancy of cancer due to migration, invasion and metastasis, and/or inhibit the growth of primary cancer cells by inhibiting HDM2 and/or HDMX activity.

The leucine zipper variant polypeptide can be part of a pharmaceutical composition. The pharmaceutical composition comprises the leucine zipper variant as an active ingredient along with a pharmaceutical additive, such as a carrier, a diluent and/or an excipient. The pharmaceutical composition may have inhibitory activity against HDM2/ HDMX and/or cancer (e.g., cancer associated with HDM2/ HDMX expression).

A pharmaceutically acceptable carrier which is typically used for drug formulations may be available for the pharmaceutical composition or the method. Examples of the carrier include lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, and mineral oil, but are not limited thereto. In addition, the pharmaceutical composition may further include a diluent, an excipient, a lubricant, a humectant, a sweetener, a flavoring agent, an emulsifier, a suspending agent, and a preservative.

The pharmaceutical composition may be administered orally or parenterally. For parenteral administration, the administration may be carried out via intravenous, subcutaneous, intramuscular, intraperitoneal, intradermal, local, intranasal, intrapulmonary, and intrarectal routes, but is not limited thereto. For oral administration, however, the pharmaceutical composition is preferably coated or formulated to protect the active ingredient from being degraded in the stomach because proteins or peptides are digested by pepsin. In addition, the administration may be performed with the aid of an instrument adapted for delivering the pharmaceutical composition to target cells.

A dose of the leucine zipper variant in the pharmaceutical composition may vary depending on various factors including the type of formulation, the patient's age, weight, and sex, the severity of the disorder being treated, diet, the time of administration, the route of administration, the rate of excretion, and sensitivity. For example, the pharmaceutically effective amount of the active ingredient in the pharmaceutical composition may range in single dose from 0.001 to 100 mg/kg, particularly from 0.01 to 100 mg/kg, and more particularly from 0.1 to 50 mg/kg, but is not limited thereto. The single dose may be formulated into a unit dose form or distributed into separate dose forms, or may be included within a multiple dose package. As used herein, the term "pharmaceutically effective amount" refers to an amount at which the active ingredient leucine zipper variant can exert a desired effect (i.e. the inhibition of MDM2 and/or MDMX, the treatment of prevention of cancer, the stimulation of p53, or combinations thereof), and may fall within the range set forth above.

The pharmaceutical composition may be formulated into solutions in oil or aqueous media, suspensions, syrup, emulsions, elixirs, powders, granules, tablets, or capsules, and in this context, a dispersant or a stabilizer may be further employed.

According to another aspect thereof; provided is a conjugate of the leucine zipper variant and HDM2, HDMX, or combination of HDM2 and HDMX. In this conjugate, HDM2, HDMX or a combination thereof may be chemically (such as, covalently (e.g., via S—S bond)) linked to both lateral sides of the leucine zipper variant to form a chemical conjugation (e.g., a covalent conjugation (e.g., via S—S bond)), that is, the external part of the hydrophobic leucine region of each alpha helix (see FIG. 8).

Another embodiment provides a method for preparing a leucine zipper variant, including substituting at least one amino acid residue on an amino acid sequence of a wild-type leucine zipper (e.g., SEQ ID NO: 1) with a different amino acid. The leucine zipper variant is characterized by high affinity to HDM2/ HDMX.

The method of preparing a leucine zipper variant may include substituting at least one amino acid residue selected from the group consisting of the amino acid residues at positions 10, 14, 15, 18, and 21 of the amino acid sequence of SEQ ID NO: 1 with a different amino acid residue. More particularly, the method may include performing substitutions at positions 10 and 15 on the amino acid sequence set forth in SEQ ID NO: 1 and optionally at, at least one of positions 14, 18 and 21, with different amino acids.

For example, the method for preparing a leucine zipper variant may include performing an amino acid substitution:
 (a) of glutamic acid (E) with glycine (G) at position 10 of the amino acid sequence set forth in SEQ ID NO: 1;
 (b) of lysine (K) with serine (S) at position 15 of the amino acid sequence set forth in SEQ ID NO: 1;
 (c) of serine (S) with phenylalanine (F) at position 14 of the amino acid sequence set forth in SEQ ID NO: 1;
 (d) of histidine (H) with tryptophan (W) at position 18 of the amino acid sequence set forth in SEQ ID NO: 1; and
 (e) of asparagine (N) with leucine (L) at position 21 of the amino acid sequence set forth in SEQ ID NO: 1.

In one embodiment, the preparing method of leucine zipper variant may include performing amino acid substitutions:
 (a) of glutamic acid (E) with glycine (G) at position 10 of the amino acid sequence set forth in SEQ ID NO: 1; and
 (b) of lysine (K) with serine (S) at position 15 of the amino acid sequence set forth in SEQ ID NO: 1.

In another embodiment, the method of preparing a leucine zipper variant may include performing amino acid substitutions:
 (a) of glutamic acid (E) with glycine (G) at position 10 of the amino acid sequence set forth in SEQ ID NO: 1; and
 (b) of lysine (K) with serine (S) at position 15 of the amino acid sequence set forth in SEQ ID NO: 1, and
 optionally performing an amino acid substitution:
 (c) of serine (S) with phenylalanine (F) at position 14 of the amino acid sequence set forth in SEQ ID NO: 1;
 (d) of histidine (H) with tryptophan (W) at position 18 of the amino acid sequence set forth in SEQ ID NO: 1;
 (e) of asparagine (N) with leucine (L) at position 21 of the amino acid sequence set forth in SEQ ID NO: 1, or
 a combination thereof.

The leucine zipper variant can be produced by other methods as well, such as by direct synthesis, or by expressing a polynucleotide encoding the leucine zipper variant in a cell to make the leucine zipper variant.

Another embodiment provides a polynucleotide encoding the leucine zipper variant, a recombinant vector comprising the polynucleotide, and a recombinant cell transformed with the recombinant vector.

The polynucleotide encoding the leucine zipper variant may encode the amino acid sequence set forth in SEQ ID NO: 2 or SEQ ID NO: 17. An example of a polynucleotide encoding a leucine zipper variant is a polynucleotide comprising the nucleotide sequence set forth in SEQ ID NO: 3.

As used herein, the term "vector" refers to a means for expressing a target gene in a host cell, as exemplified by a plasmid vector, a cosmid vector, and a viral vector such as a bacteriophage vector, adenovirus vector, retrovirus vector, and an adeno-related virus vector. The recombinant vector may be constructed from, but not limited to, well-known plasmids (for example, pSC101, pGV1106, pACYC177, ColE1, pKT230, pME290, pBR322, pUC8/9, pUC6, pBD9, pHC79, pIJ61, pLAFR1, pHV14, pGEX series, pET series, pUC19, etc.), phages (for example, λgt4λB, λ-Charon, λΔz1, M13, etc.) or viruses (for example, SV40, etc.) by manipulation.

In the recombinant vector, the polynucleotide coding for the protein conjugate may be operatively linked to a promoter. The term "operatively linked" is intended to pertain to a functional linkage between a nucleotide sequence of interest and an expression regulatory element (for example, a promoter sequence) so that the expression of the nucleotide sequence of interest is governed by the regulatory element. For instance, when it is "operatively linked" to the regulatory element, the nucleotide sequence of interest can be transcribed and/or translated under the control of the regulatory element.

The recombinant vector may be constructed as a cloning vector or an expression vector. For recombinant expression vectors, a vector typically available for expressing a foreign protein in plant, animal or microorganism cells may be employed. Various methods well known in the art may be used for the construction of recombinant vectors.

For use in hosts, such as prokaryotic or eukaryotic cells, the recombinant vector may be constructed appropriately. For example, when a vector is constructed as an expression vector for use in a prokaryotic host, the vector typically includes a strong promoter for transcription (e.g., a pLλ promoter, a CMV promoter, a trp promoter, a lac promoter, a tac promoter, a T7 promoter, etc.), a ribosomal binding side for initiating translation, and transcriptional/translational termination sites. On the other hand, an expression vector for use in a eukaryotic host includes an origin of replication operable in a eukaryotic cell, such as a f1 origin of replication, an SV40 origin of replication, a pMB1 origin of replication, an adeno origin of replication, an AAV origin of replication, a BBV origin of replication. In addition, the expression vector typically includes a promoter derived from mammalian cells (for example, metallothionein promoter) or from mammalian viruses (for example, adenovirus late promoter, vaccinia virus 7.5K promoter, SV40 promoter, cytomegalovirus promoter and tk promoter of HSV), and a polyadenylation sequence as a transcription termination sequence.

The recombinant cell may be prepared by introducing the recombinant vector into a suitable host cell. So long as it allows for the sequential cloning and expression of the recombinant vector in a stable manner, any host cell known in the art may be employed in the present invention. Examples of the prokaryotic host cell available for the present invention include *E. coli* JM109, *E. coli* BL21, *E. coli* RR1, *E. coli* LE392, *E. coli* B, *E. coli* X 1776, *E. coli* W3110, *Bacillus* spp. such as *Bacillus subtilis* and *Bacillus thuringiensis*, and enterobacteriaceae strains such as *Salmonella typhimurium, Serratia marcescens* and various *Pseudomonas* species. Eukaryotic host cells to be transformed may be *Saccharomyce cerevisiae*, insect cells, and animal cells including, but not limited to Sp2/0, CHO (Chinese hamster ovary) K1, CHO DG44, PER.C6, W138, BHK, COS-7, 293, HepG2, Huh7, 3T3, RIN, and MDCK.

Using a method well known in the art, the polynucleotide or a recombinant vector carrying the polynucleotide may be introduced (incorporated) into a host cell. This transformation is carried out by any suitable technique, such as through $CaCl_2$ or electroporation when the host cell is prokaryotic. For eukaryotic host cells, the genetic introduction may be achieved using, but not limited to, microinjection, calcium phosphate precipitation, electroporation, liposome-mediated transfection, or particle bombardment.

To select a (recombinant vector) transformed host cell, advantage may be taken of the phenotype attributed to a selection marker according to a method known in the art. For example, when the selection marker is a gene resistant to a certain antibiotic, the host cells may be grown in the presence of the antibiotic in a medium to select a transformant of interest.

The leucine zipper variant of the present invention is applicable to the treatment of diseases related to the activation of HDM2/ HDMX due its excellent ability to bind HDM2/ HDMX. When conjugated with a cell-penetrating peptide, the leucine zipper variant can exhibit improved delivery into cancer cells.

EXAMPLES

Hereafter, the present invention will be described in detail by examples.

The following examples are intended merely to illustrate the invention and are not construed to restrict the invention.

Example 1

Construction of Leucine Zipper Variant

Design processes for constructing leucine zipper variants are illustrated in Tables 1A, 1B, and FIG. 1:

TABLE 1A

|  |  | 1st repeat |  |  |  |  |  |  | 2nd repeat |  |  |  |  |  |
|---|---|---|---|---|---|---|---|---|---|---|---|---|---|---|
| Heptad position |  | a | b | c | d | e | f | g | a | b | c | d | e | f | g |
| Residue No. | 1 | 2 | 3 | 4 | 5 | 6 | 7 | 8 | 9 | 10 | 11 | 12 | 13 | 14 | 15 |
| GCN4LZ | R | M | K | Q | L | E | D | K | V | E | E | L | L | S | K |
| p53LZ1 | R | M | K | Q | L | E | D | L | V | E | E | L | L | F | K |
| p53LZ2 | R | M | K | Q | L | E | D | K | V | G | E | L | L | F | S |
| p53LZ3 | R | M | K | Q | L | E | D | K | V | S | E | L | L | F | A |
| pMI |  |  |  |  |  |  |  |  |  |  |  | T | S | F | A |
| SAH-p53-8 |  |  |  |  |  |  |  |  | Q | S | Q | Q | T | F | X |
| p53TAD |  |  |  |  |  |  |  |  | S | Q | E | T | F | S |  |

TABLE 1B

|  | 3rd repeat | | | | | | | 4th repeat | | | | | | | |
|---|---|---|---|---|---|---|---|---|---|---|---|---|---|---|---|
| Heptad position | a | b | c | d | e | f | g | a | b | c | d | e | f | g | a |
| Residue No. | 16 | 17 | 18 | 19 | 20 | 21 | 22 | 23 | 24 | 25 | 26 | 27 | 28 | 29 | 30 |
| GCN4LZ | N | Y | H | L | E | N | E | V | A | R | L | K | K | L | V |
| p53LZ1 | N | Y | W | L | E | L | E | V | A | R | L | K | K | L | V |
| p53LZ2 | N | Y | W | L | E | L | E | V | A | R | L | K | K | L | V |
| p53LZ3 | E | Y | W | L | L | L | S | V | T | R | L | K | K | L | V |
| pMI | E | Y | W | A | L | L | S | | | | | | | | |
| SAH-p53-8 | N | L | W | R | L | L | X | Q | N | | | | | | |
| p53TAD | D | L | W | K | L | L | P | E | N | | | | | | |

Both the 1st and the 4th repeat of GCN4LZ (SEQ ID NO: 1) were excluded from mutation because they are terminal regions and a mutation thereof is highly apt to change overall stability of the protein. Particular attention was paid to the 4th repeat of GCN4LZ since it is a trigger site responsible for GCN4LZ folding. Therefore, the search for mutation targets was focused on the 2nd and the 3rd repeat of GCN4LZ. Inter alia, f and c sites, located on the GCN4LZ surface area, were found to be places where F, W and L amino acid residues, critical for binding to HDM2 and/or HDMX, are optimally grafted (in full consideration of amino acid sequence & 3D structure alignment between GCN4LZ, WT p53, pMI, SAH-p53-8).

In this procedure, the leucine zipper variant p53LZ1 (Comparative Example 1) of Table 1 was constructed. However, superimposition of X-ray crystal structures of WTp53-HDM2 complex and pMI-HDM2 complex on GCN4LZ suggested that a more intense protein-protein interaction would occur when E10 and K15 of GCN4LZ are substituted with smaller amino acids (that is, less hindrance between two proteins). In response to this analysis, E10 and K15 were substituted with G and S, respectively, to construct a leucine zipper variant, p53LZ2. p53LZ2 was observed to have higher affinity to HDM2 and HDMX, compared to p53LZ1, as demonstrated in the following in vitro assay.

In addition, p53LZ3 (Comparative Example 2) of Table 1, which was constructed to have an amino acid sequence similar to that of pMI, known as an HDM2 & HDMX high affinity peptide by peptide phage display, was analyzed for affinity to HDM2 and HDMX. As shown in the following in vitro binding assay, p53LZ3 bound to neither HDM2 nor HDMX.

The leucine zipper variants p53LZ1 (Comparative Example 1), p53LZ2 (Inventive), and p53LZ2 (Comparative Example 2) were used in the following Examples.

Example 2

Binding Assay 1 of Leucine Zipper Variants to HDM2/HDMX

To quantitatively analyze the binding of the leucine zipper variants to HDM2/ HDMX, in vitro GST pull-down assay was performed. Briefly, purified proteins tagged with GST (produced from GST cds inserted into pGEX-4T3 vector, GE Healthcare), that is, GST-p53LZ1, GST-p53LZ2, GST-p53LZ3, HDM2NTD (N-terminal domain; consisting of amino acids at positions 1 to 125 of NP_002383), HDMX-NTD (consisting amino acid residues at positions 1 to 132 of NP_001191100) were made to be in the equal PBS buffer (pH7.4, Gibco) (dialysis for overnight at 4° C.). Each of the GST-tagged proteins was mixed with at a molar ratio of 1:2 with HDM2NTD or HDMXNTD, and incubated at 4° C. for 1 hr. Thereafter, the GST-labeled proteins mixed with HDM2NTD or HDMXNTD were pulled-down using 20 µL (microliter) of glutathione resins (GE Healthcare).

For this pull-down assay, the protein mixtures were incubated with 20 µL of GSH resins at 4° C. for 1 hr to immobilize the GST-tagged proteins to the GSH resins.

Figure 2:
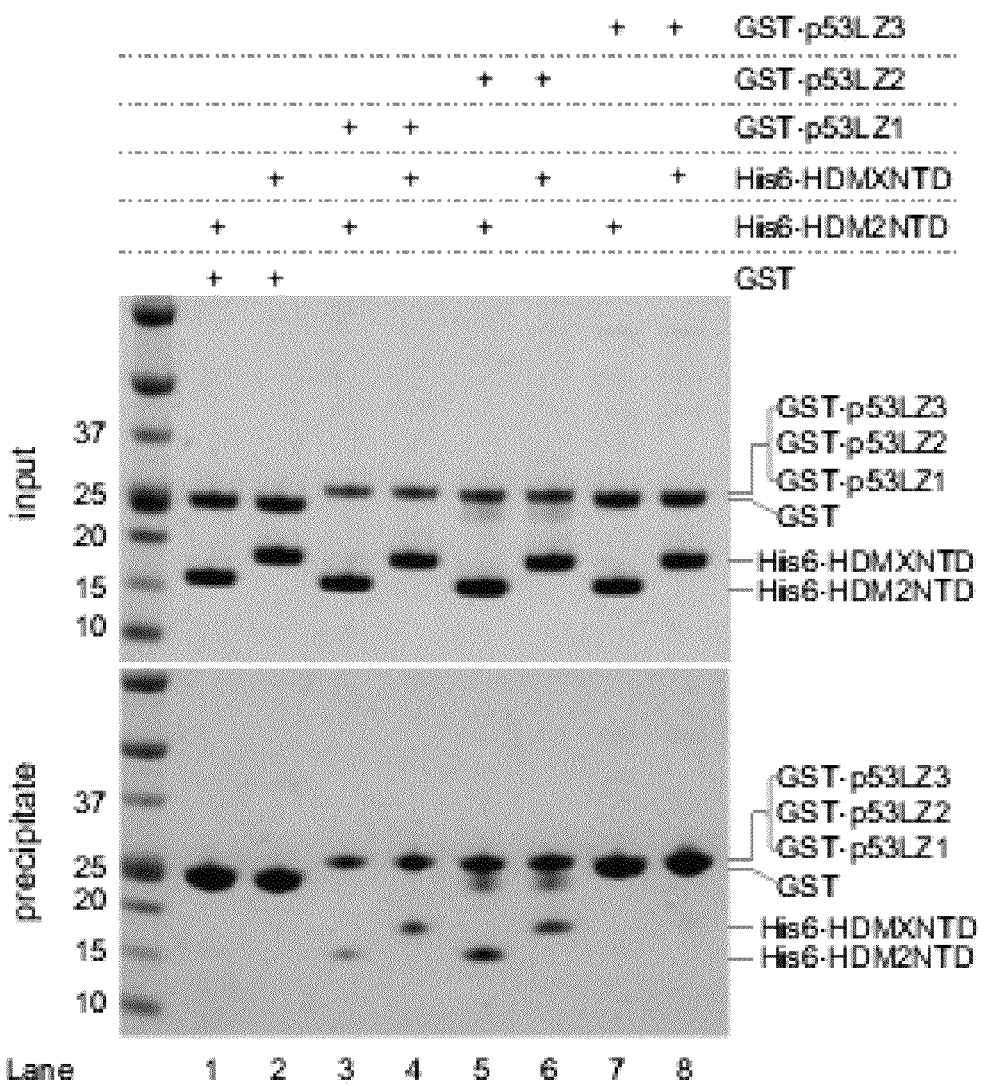
FIG. 2 displays the results of an in vitro binding assay of leucine zipper variants and HDM2/ HDMX, as measured by GST-pull downs.

The resins were washed three times with 500 µL of PBS (pH 7.4) to remove proteins which were not attached thereto. After the proteins were eluted with SDS sample buffer, the eluates were analyzed by 12% SDS-PAGE (Invitrogen). The results are shown in FIG. 2. As is apparent from data of FIG. 2, HDM2NTD and HDMXNTD were each observed to bind to both GST-p53LZ1 and GST-p53LZ2, but not to either GST or GST-p53LZ3. These results demonstrate that HDM2NTD or HDMXNTD more strongly binds to p53LZ2 than to p53LZ1.

Example 3

Binding Assay 2 of Leucine Zipper Variants to HDM2/HDMX

Figure 3:
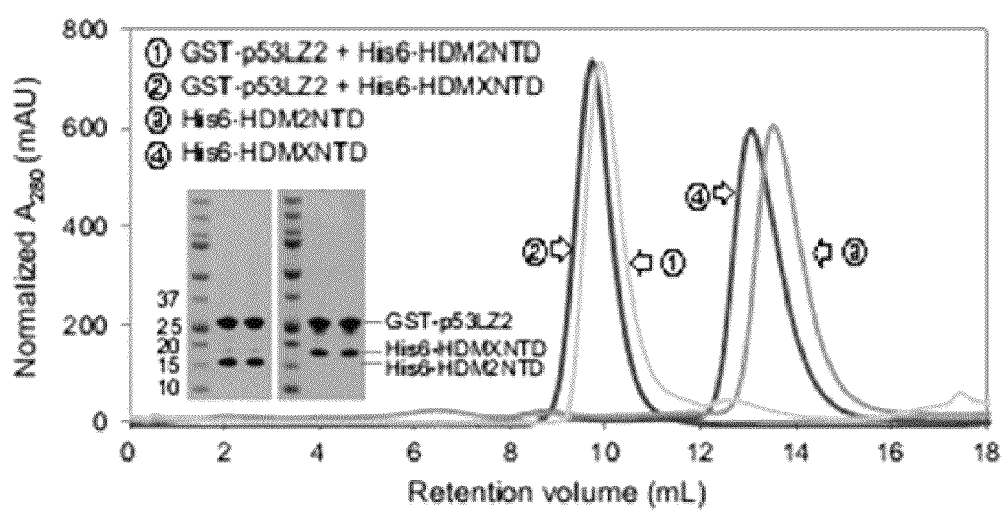
FIG. 3 is a graph displaying results from an in vitro binding assay of leucine zipper variants and HDM2/ HDMX, as measured by analytical size-exclusion chromatography (SEC).

GST-p53LZ2 was mixed at a molar ratio of 1:1 with His6-HDM2NTD or His6-HDMXNTD and incubated overnight at 4° C. Size-exclusion chromatography (column: 10/300 superdex-75gl (GE healthcare), buffer=1×PBS pH 7.4, temperature=18° C.) was followed by SDS-PAGE. Retention volumes were monitored since a complex would be eluted at a lower volume than the retention volume of individual HDM2NTD or HDMXNTD. The results are shown in FIG. 3. As can be seen in FIG. 3, GST-p53LZ2, when mixed with HDM2NTD or HDMXNTD, was eluted at lower retention volumes, compared to HDMXNTD or HDMXNTD alone (for use as a control, HDM2NTD or HDMXNTD was not mixed with GST-p53LZ2, but was incubated alone under the same condition before analytical SEC).

Example 4

Binding Assay 3 of Leucine Zipper Variants to HDM2/HDMX (Comparison with p53)

To examine the affinity of GST-WT p53TAD (NP_000537.3, NM_000546.5; SEQ ID NO: 4: MEEPQS-DPSV EPPLSQETFS DLWKLLPENN VLSPLPSQAM DDLMLSPDDI EQWFTEDPGP DEAPRMPEAA PP (72a.a.)), GST-p53LZ1, GST-p53LZ2, GST, pDIQ (ETFEH-WWSQLLS: SEQ ID NO: 15) and pMI (TSFAEYWNLLSP; SEQ ID NO: 16) for HDM2/ HDMX, ELISA was carried out.

HDM2 or HDMX was diluted to a concentration of 20 µg/ml in a coating buffer (pH 9.6; 0.05M carbonate-bicarbonate buffer, pH 9.6 (Sigma-Aldrich)), applied to 96-well plates (Nunc, Maxisorp) and incubated overnight at 4° C. Then, the plates were treated with 300 µl of 3% skim milk w/PBS-T (room temperature, 3 hrs) to block the binding of other proteins. The 96-well plates were washed with 200 µL of PBS-T before each well was treated with serial dilutions of 0, 50, 100, 200, 400, 800, 1200, 1600, 2400, 3200, 4800, and 6400 nM of GST-WT p53, GST-p53LZ1, GST-p53LZ2, GST, pDIQ, and pMI.

After one hour of incubation, the plates were washed three times with 300 µL of PBS-T, and incubated at room temperature for 1 hr with 100 µL of an HRP conjugated-anti-GST antibody (Abcam, 1:2000). Thereafter, treatment with TMB substrate (Pierce, 100 µL) for 5 min developed a color. A stop solution (Pierce, 100 µL) was added, followed by reading absorbance at 450 nm on microwell reader (Molecular Device, Model: 340PC384).

Figure 4A:
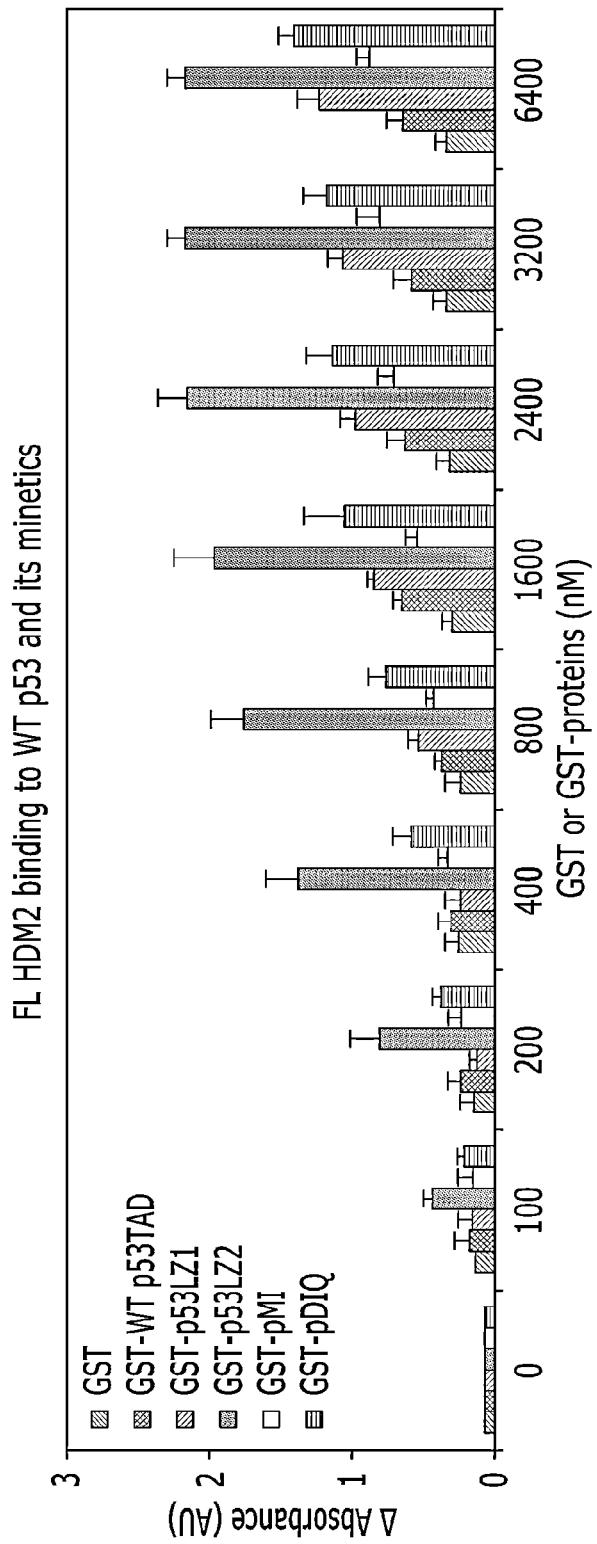
FIG. 4A is a graph displaying ELISA results which demonstrate the difference between the leucine zipper variant and p53 (wild-type) affinity to full-length HDM2.
Figure 4B:
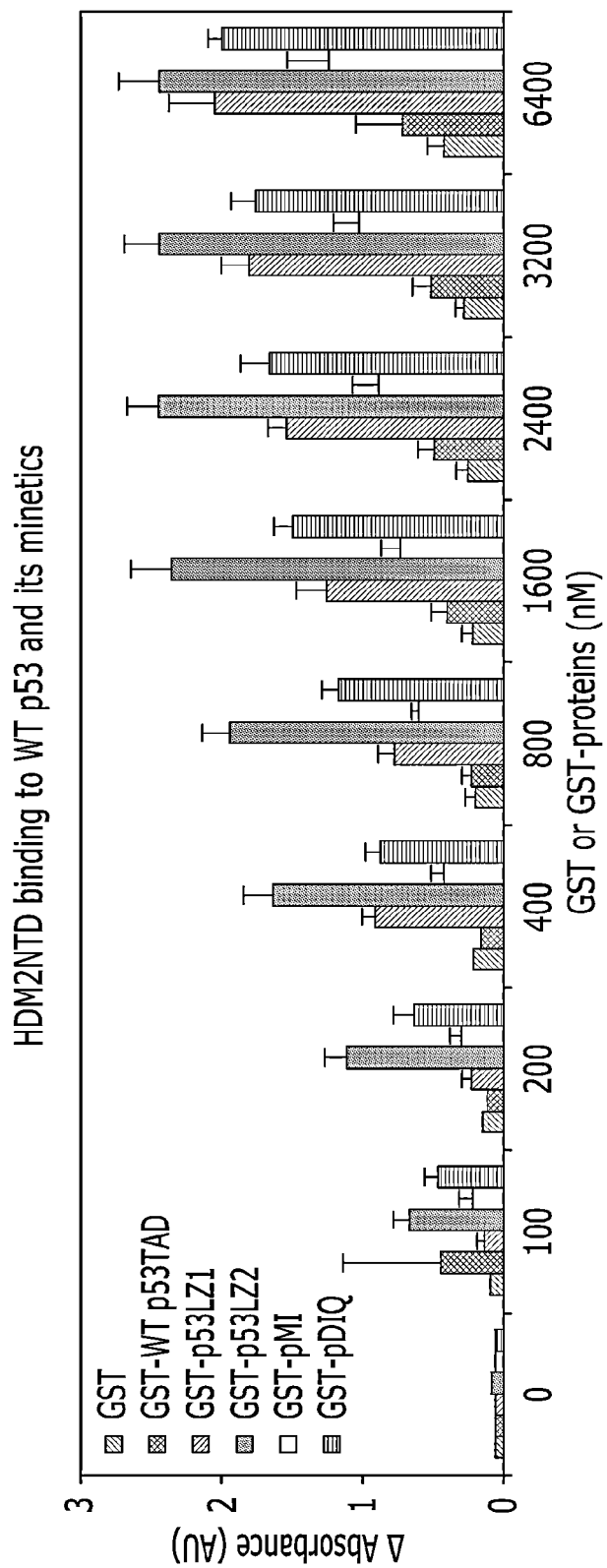
FIG. 4B is a graph displaying ELISA results which demonstrate the difference between the leucine zipper variant and p53 (wild-type) affinity to HDM2-NTD (N-terminal domain).
Figure 4C:
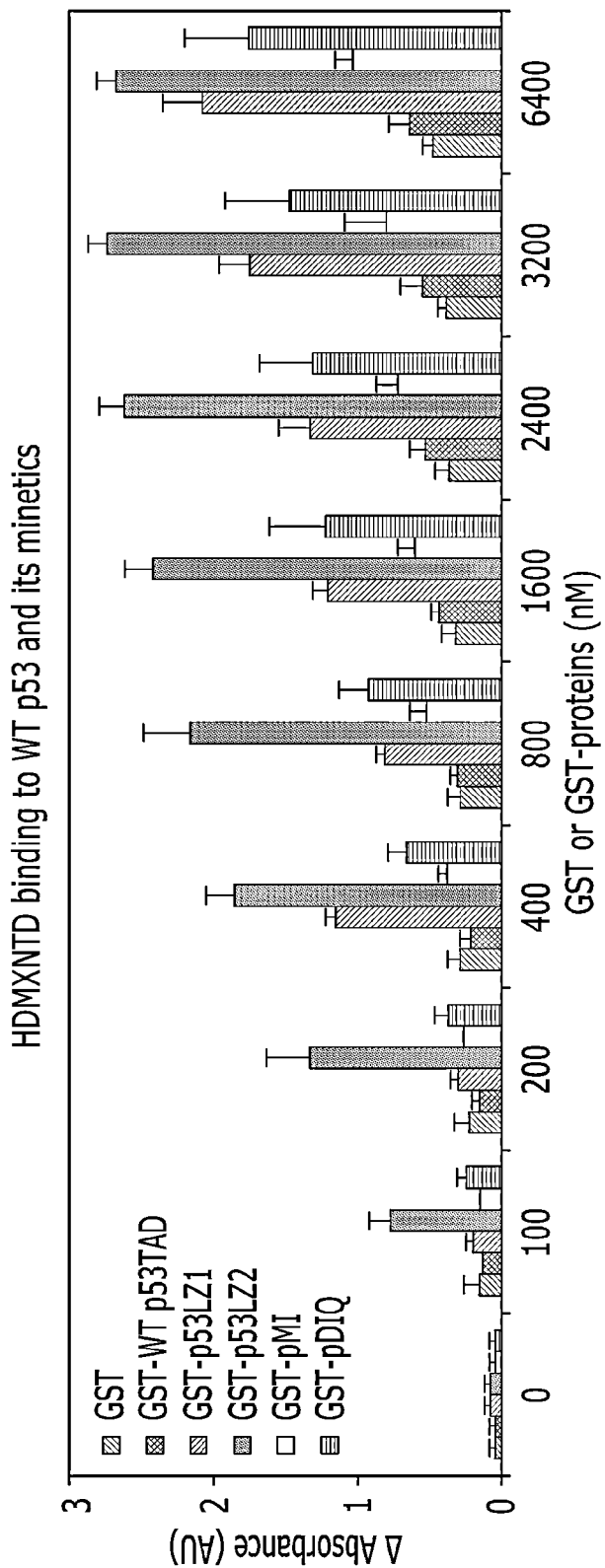
FIG. 4C is a graph displaying ELISA results which demonstrate the difference between the leucine zipper variant and p53 (wild-type) affinity to HDMX-NTD.

The results are given in FIGS. 4A-4C. In FIGS. 4A-4C, affinities of the proteins are depicted for full-length HDM2 (4A), HDM2-NTD (N-terminal domain) (4B), and HDMX-NTD (4C). As can be seen in FIGS. 4A-4C, the affinity of p53LZ2 for HDM2 and HDMX is far superior to that of p53 or that of the other mimetics, indicating that p53LZ2 victoriously competes with p53 for binding HDM2 and HDMX, and can effectively the HDM2- or HDMX-mediated proteosomal degradation of p53.

Meanwhile, the binding of p53LZ2 to HDM2 and HDMX was evaluated by ITC (isothermal titration calorimetry). To this end, 370 µL of 0.03 mM HDM2NTD (PBS, pH 7.4) was added to the cell of auto-ITC (GE Healthcare) and titrated with 110 µL of 0.5 mM p53LZ2 (PBS, pH 7.4) using a syringe (injection volume=3 µL, injection time=6 s, delay time=150 s, temperature=18° C., total 20 times injected) to calculate Kd values from temperature differences between the ITC reference cell and the sample cells.

Figure 5:
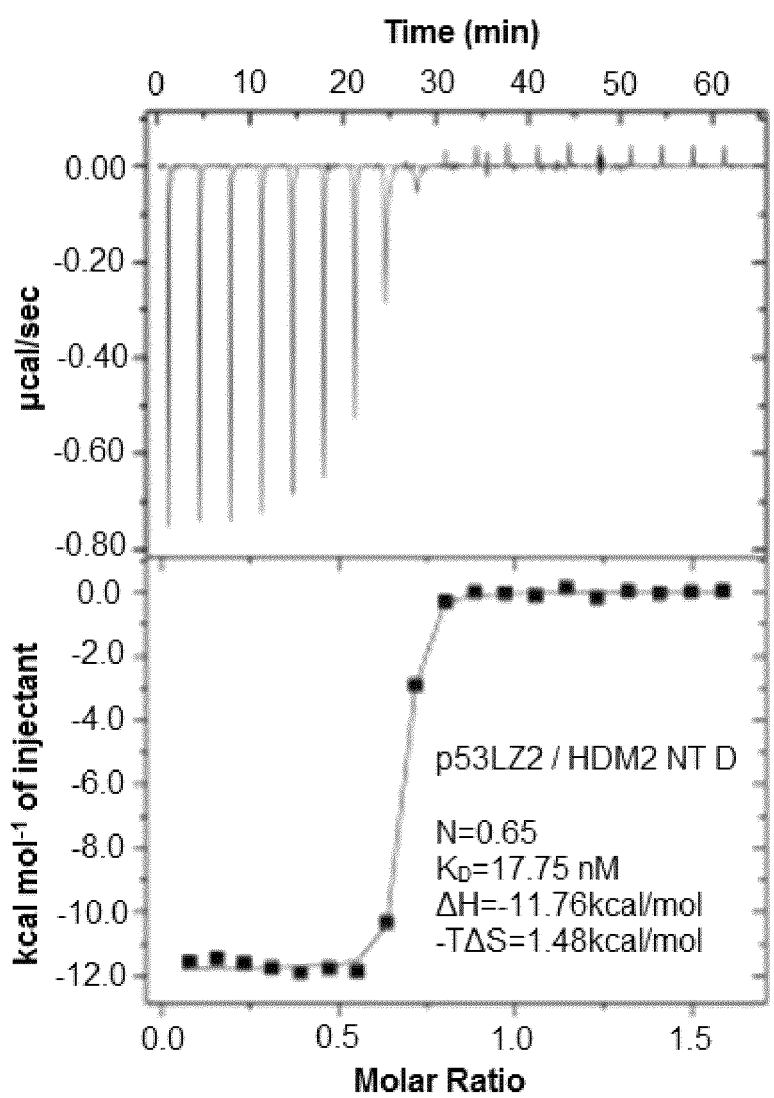
FIG. 5 provides graphs demonstrating the affinity of the leucine zipper variant p53LZ2 according to one embodiment for HDM2NTD, as measured by ITC (isothermal titration calorimetry).
Figure 6:
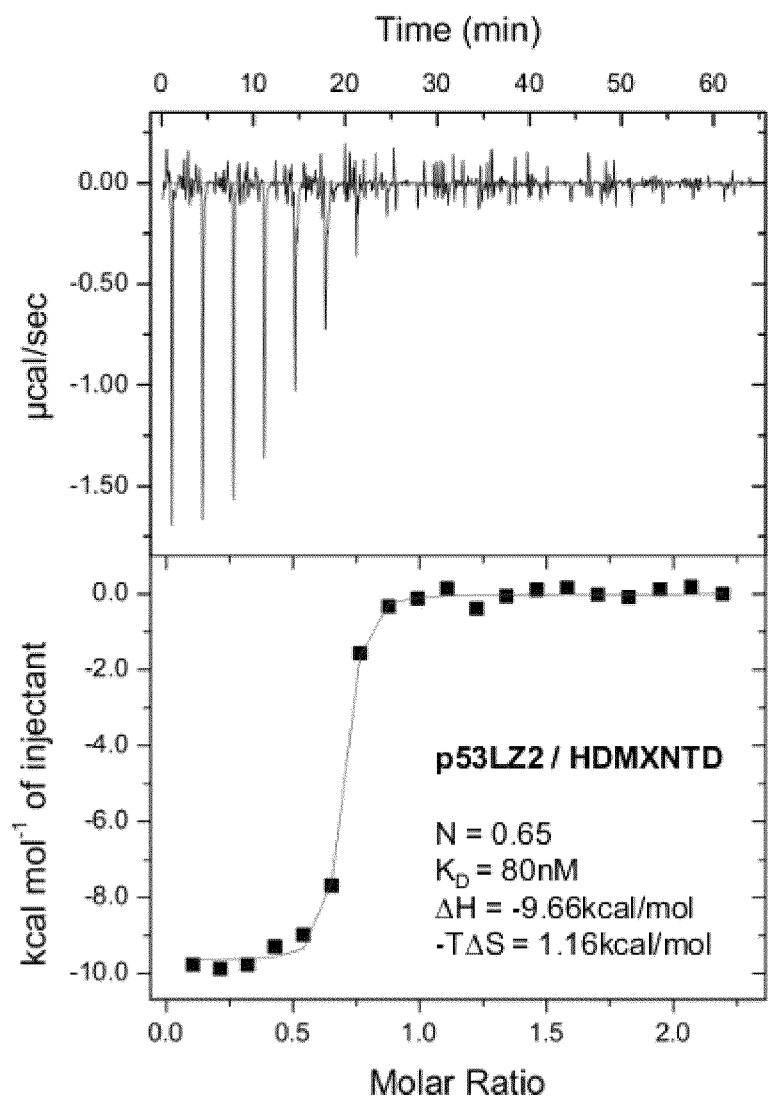
FIG. 6 provides graphs demonstrating the affinity of the leucine zipper variant p53LZ2 according to one embodiment for HDMXNTD, as measured by ITC (isothermal titration calorimetry).

Results are given in FIG. 5 (HDM2NTD) and FIG. 6 (HDMXNTD). As shown in FIGS. 5 and 6, p53LZ2 has an affinity (Kd) of approximately 18 nM (17.75 nM) for HDMXNTD and of approximately 80 nM for HDMXNTD.

Example 5

Three-Dimensional Structure Analysis of Leucine Zipper Variants

Figure 7:
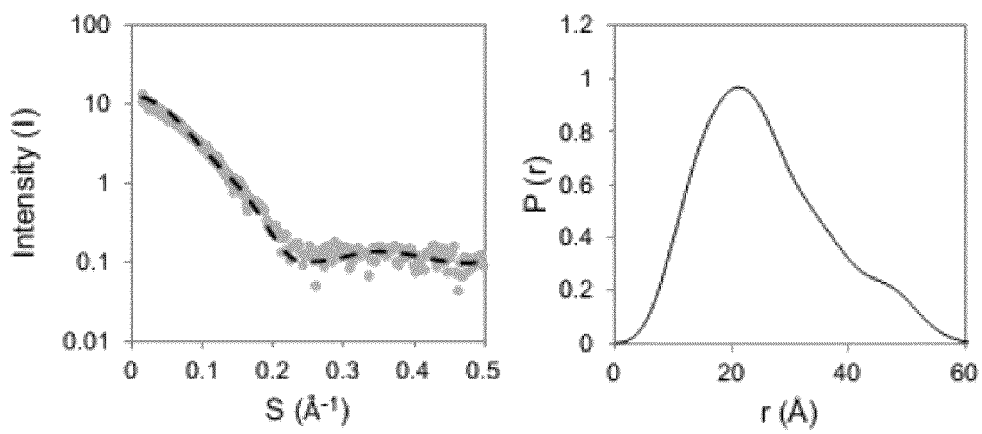
FIG. 7 shows a one-dimensional scattering pattern detected from the leucine zipper variant p53LZ2-HDM2NTD complex in a solution (PBS, pH 7.4) when exposed to X-ray (left panel), and the protein size (maximum of dimension=Dmax) calculated by reduction of the one-dimensional data obtained from the X-ray scattering using P(r) function.

One-dimensional scattering patterns were obtained by exposing a p53LZ2-HDM2NTD complex (PBS, pH 7.4 at 18° C.) in a solution status to X-ray using 4C SAXS II beamline, at the Pohang Accelerator Laboratory. The results are depicted in FIG. 7 (left). Raw data obtained are plotted in the left panel of FIG. 7 wherein dotted lines account for calculated values for theoretical scattering patterns of the PDB structure of the p53LZ2-HDM2NTD complex. The PDB structure of the p53LZ2-HDM2NTD complex was analyzed through X-ray crystallography and comparative modeling. Theoretical values were calculated using the program Crysol (www.embl-hamburg.de/biosaxs). As is apparent from FIG. 7, practical raw data is coincident with the theoretical data.

By one-dimensional data reduction, the P(r) function is obtained to describe the size of protein (maximum of dimension=Dmax). The P(r) function accounting for the size of protein (maximum of dimension=Dmax) was calculated by reduction of the 1D data obtained by X-ray scattering. The results are given in the right panel of FIG. 7. P(r) function (www.biosis.net/tutorial/5) describes the paired-set of all distances between electron points within an object protein or protein complex. It is used to determine conformational changes, and dimensions of proteins and protein complexes.

Figure 8:
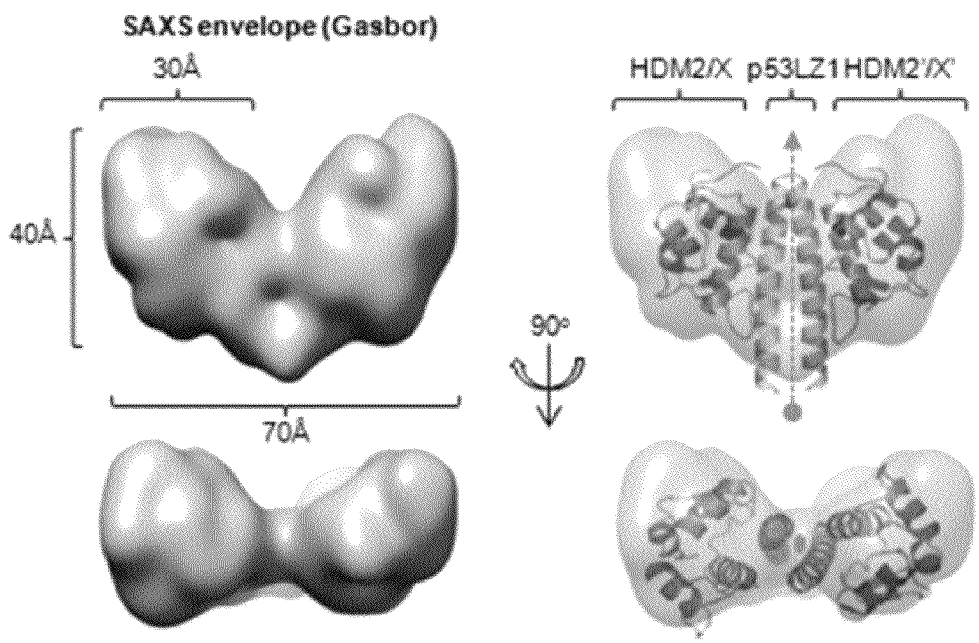
FIG. 8 illustrates three dimensional conformations of the leucine zipper variant p53LZ2-HDM2/ X complex, as detected by SAXS analysis.

Solution conformations of the p53LZ2-HDM2NTD complex were contoured from the data of FIG. 7 using GASBOR (www.embl-hamburg.de/biosaxs), and the results are given in FIG. 8, showing the figures of the p53LZ2-HDM2NTD complex in a solution at low resolutions. In addition, there is a correlation between the p53LZ2-HDM2NTD complex model and the solution conformation obtained by fitting the model into the GASBOR envelope.

Example 6

Assay for Inhibitory Activity of Leucine Zipper Variants against Cancer Cell Growth The leucine zipper variant p53LZ2 was evaluated for anticancer activity against the osteosarcoma cell line SJSA-1 (ATCC), the breast cancer cell line MCF7 (ATCC), and the skin cancer cell line A-431 (ATCC), the first two expressing wild-type p53 and the other expressing mutant p53.

Each of the cell lines was seeded at a density of $1 \times 10^3$ cells/well in 10% FBS-supplemented RPMI (Gibco) or DMEM (Gibco) into 96-well plates. The next day, the leucine zipper variant (TAT-p53LZ2; TAT (RKKRRQRRR; SEQ ID NO: 5) linked to the N-terminus of p53LZ2, constructed in Example 1) or Nutlin-3 (Sigma) was added at a concentration of 0, 0.59, 0.88, 1.32, 1.98, 2.96, 4.44, 6.67, 10, or 15 µM (increasing by 1.5 fold) in an amount of 100 µL to each well before the cells were cultured for 5 days at 37° C. in an 5% $CO_2$ incubator. To each well was added 80 µL of CellTiter-Glo reagent (Promega), followed by measuring luminescence on EnVision Multilabel Reader (PerkinElmer) to examine cell viability.

Figure 9:
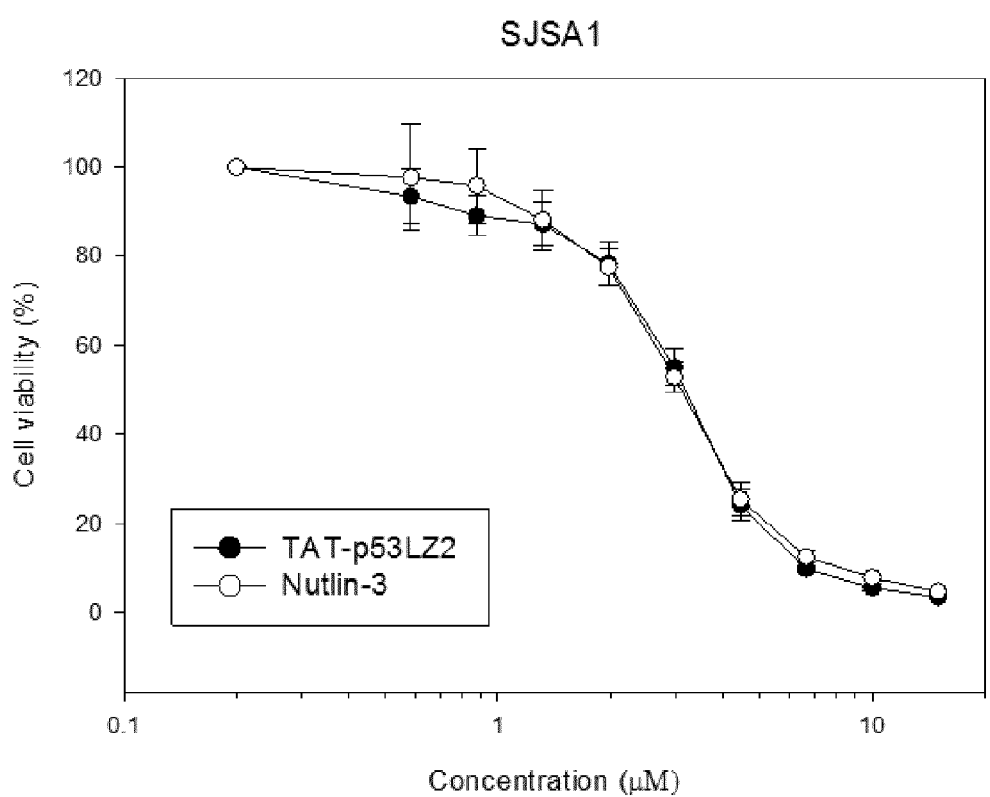
FIG. 9 is a graph displaying the anticancer activity of the TAT-leucine zipper variant p53LZ2 against the SJSA-1 cell line.
Figure 10:
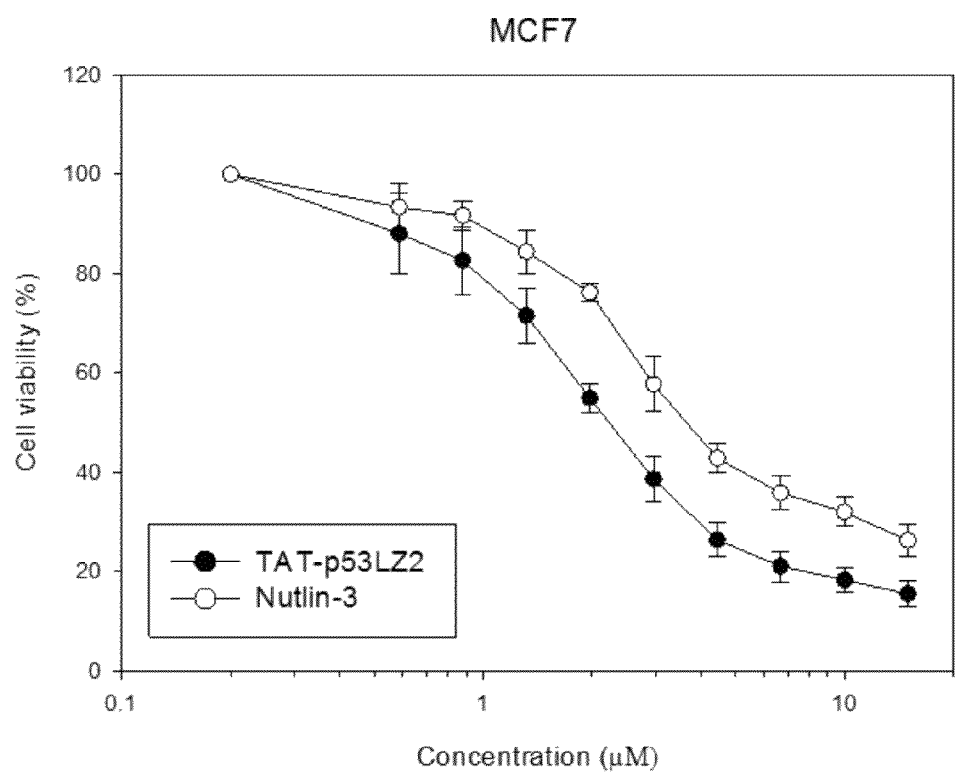
FIG. 10 is a graph displaying the anticancer activity of the TAT-leucine zipper variant p53LZ2 against the MCF7 cell line.
Figure 11:
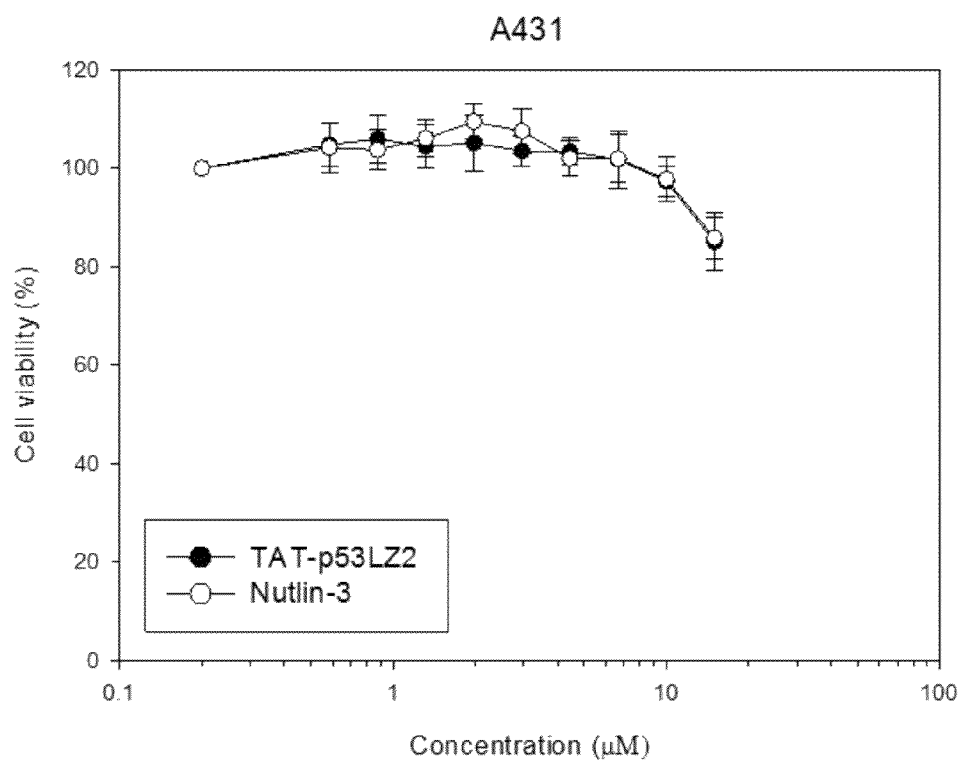
FIG. 11 is a graph displaying the anticancer activity of the TAT-leucine zipper variant against the A431 cell line.

The results are given in FIGS. 9 to 11 (FIG. 9: SJSA-1 cell line, FIG. 10: MCF7 cell line, FIG. 11: A431 cell line). As shown in FIGS. 9 and 10, TAT-p53LZ2 and Nutlin-3 exhibited 90% or higher anticancer effects at the maximum concentration on SJSA-1 while TAT-p53LZ2 was 10% higher in anticancer activity against MCF7 cell line than Nutlin-3. In the A431 cell line where p53 reactivation was impossible because of mutant p53 expression, both TAT p53LZ2 and Nutlin-3 failed to exert cytotoxicity, implying that the leucine zipper variant inhibits the growth of cancer cells in a p53-dependent mechanism, like Nutlin-3. In addition, the leucine zipper variant p53LZ2 was observed to have anticancer activity as high as or higher than that of the positive control Nutlin.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A leucine zipper polypeptide variant comprising SEQ ID NO: 1 with at least one amino acid substitution selected from the group consisting of
   (a) substitution of glutamic acid (E) with glycine (G) at position 10;
   (b) substitution of lysine (K) with serine (S) at position 15;
   (c) substitution of serine (S) with phenylalanine (F) at position 14;
   (d) substitution of histidine (H) with tryptophan (W) at position 18; and (e) substitution of asparagine (N) with leucine (L) at position 21.

2. The leucine zipper polypeptide variant of claim 1 comprising the following substitutions:
   (a) substitution of glutamic acid (E) with glycine (G) at position 10; and
   (b) substitution of lysine (K) with serine (S) at position 15.

3. The leucine zipper polypeptide variant of claim 2, further comprising at least one substitution selected from the group consisting of:
   (c) substitution of serine (S) with phenylalanine (F) at position 14;
   (d) substitution of histidine (H) with tryptophan (W) at position 18; and
   (e) substitution of asparagine (N) with leucine (L) at position 21.

4. The leucine zipper polypeptide variant of claim 1, wherein the leucine zipper variant comprises SEQ ID NO: 2.

5. The leucine zipper polypeptide variant claim 1, further comprising a cell-penetrating peptide selected from the group consisting of: SEQ ID NO: 5, SEQ ID NO: 6, a cell-penetrating peptide fragment of SEQ ID NO: 6 including 7 to 16 consecutive amino acids of SEQ ID NO: 6, and a fusion peptide of SEQ ID NO: 6 or a cell-penetrating peptide fragment of SEQ ID NO: 6 including 7 to 16 consecutive amino acids and one of SEQ ID NO: 9, SEQ ID NO: 10, SEQ ID NO: 11, SEQ ID NO: 12, or SEQ ID NO: 13.

6. A polynucleotide encoding the leucine zipper polypeptide variant of claim 1.

7. The polynucleotide of claim 6 wherein the polynucleotide comprises SEQ ID NO: 3.

8. A recombinant vector comprising the polynucleotide of claim 6.

9. A recombinant cell transformed with the recombinant vector of claim 8.

10. A pharmaceutical composition comprising the leucine zipper polypeptide variant of claim 1 and a carrier.

11. A method of inhibiting human double minute 2 homolog (HDM2) or human double minute four homolog (HDMX in a subject), comprising administering the leucine zipper polypeptide variant of claim 1 to a subject.

12. A method of preventing or treating a cancer comprising administering the leucine zipper polypeptide variant of claim 1 to a subject in need thereof.

13. The method of claim 12, wherein the cancer is selected from the group consisting of squamous cell carcinoma, small-cell lung cancer, non-small-cell lung cancer, adrenocarcinoma of lung, squamous cell carcinoma of lung, peritoneal cancer, skin cancer, skin or intraocular melanoma, rectal cancer, perianal cancer, esophagus cancer, small intestine cancer, endocrine gland cancer, parathyroid cancer, adrenal cancer, soft-tissue sarcoma, urethral cancer, chronic or acute leukemia, lymphocytic lymphoma, hepatoma, gastrointestinal cancer, gastric cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, kidney cancer, prostate cancer, vulvar cancer, thyroid cancer, head or neck cancer, brain cancer, osteosarcoma, and a combination thereof.

14. A conjugate comprising (1) the leucine zipper polypeptide variant of claims 1 and (2) HDM2, HDMX, or a combination thereof.

15. A method for preparing a leucine zipper variant, the method comprising at least one selected from:
   (a) substituting glutamic acid (E) with glycine (G) at position 10 of SEQ ID NO: 1;
   (b) substituting lysine (K) with serine (S) at position 15 of SEQ ID NO: 1;
   (c) substituting serine (S) with phenylalanine (F) at position 14 of SEQ ID NO: 1;
   (d) substituting histidine (H) with tryptophan (W) at position 18 of SEQ ID NO: 1; and
   (e) substituting asparagine (N) with leucine (L) at position 21 of SEQ ID NO: 1.

16. The leucine zipper polypeptide variant of claim 1, wherein the leucine zipper variant binds HDM2 or HDMX at a Kd from about 0.1 nM to about 100 nM.

17. A method for producing a leucine zipper polypeptide variant of claim 1 comprising expressing a polynucleotide encoding the leucine zipper polypeptide variant in a cell.

18. A leucine zipper polypeptide variant comprising SEQ ID NO: 17, wherein Xaa at position 10 is glycine (G) or glutamic acid (E); Xaa at position 15 is serine (S) or lysine (K); Xaa at position 14 is phenylalanine (F) or serine (a); Xaa at position 18 is tryptophan (W) or histidine; and/or Xaa at position 21 is leucine (L) or asparagine (N).

19. The leucine zipper variant of claim 18, wherein
   Xaa at position 10 is glycine (G);
   Xaa at position 14 is phenylalanine (F);
   Xaa at position 15 is serine (S);
   Xaa at position 18 is tryptophan (W); and/or
   Xaa at position 21 is leucine (L).

* * * * *